United States Patent
Bernhardt et al.

(10) Patent No.: US 8,542,894 B2
(45) Date of Patent: Sep. 24, 2013

(54) METHOD AND DEVICE FOR POST-PROCESSING MEASURED VALUES REGISTERED BY WAY OF AN IMAGING SYSTEM

(75) Inventors: Dominik Bernhardt, Hausen (DE); Michael Scheuering, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 423 days.

(21) Appl. No.: 12/827,275

(22) Filed: Jun. 30, 2010

(65) Prior Publication Data

US 2011/0007953 A1 Jan. 13, 2011

(30) Foreign Application Priority Data

Jul. 9, 2009 (DE) .......................... 10 2009 032 442

(51) Int. Cl.
*G06K 9/00* (2006.01)

(52) U.S. Cl.
USPC .......................................... 382/128; 600/476

(58) Field of Classification Search
USPC ....................................................... 382/128
See application file for complete search history.

(56) References Cited

U.S. PATENT DOCUMENTS

| 8,190,244 B2 * | 5/2012 | Rollins et al. ................. 600/476 |
| 2004/0193036 A1 | 9/2004 | Zhou et al. |
| 2006/0247544 A1 | 11/2006 | Qazi et al. |
| 2008/0077032 A1 | 3/2008 | Holmes et al. |

FOREIGN PATENT DOCUMENTS

WO   WO 2008013497 A1   1/2008

OTHER PUBLICATIONS

Rebelo et al., Functional bull's eye based on three dimensional velocity information to quantify left ventricle motion in gated-SPECT, Vancouver, British Columbia, Canada, Aug. 20-24, 2008.*
Cios et al., Hybrid Intelligence System for diagnosing Coronary Stenosis, Nov./Dec. 1994, IEEE Engineering in Medicine and Biology, pp. 723-729.*
De Sá Rebelo, M. et al., "Functional bull's eye based on three dimensional velocity information to quantify left ventricle motion in gated-SPECT", In: IEEE EMBS Conf., Vancouver, Canada, Aug. 20-24, 2008, S.209-213; Others; 2008.
Cios, K. J. et al., "Hybrid Intelligence System for Diagnosing Coronary Stenosis", In: IEEE Engineering in Medicine and Biology, Nov./ Dez. 1994, S. 723-729; Others; 1994.

* cited by examiner

*Primary Examiner* — Hiep V Nguyen
(74) *Attorney, Agent, or Firm* — Harness, Dickey & Pierce (57) ABSTRACT

A method is disclosed for post-processing measured values of a tissue region including at least part of a heart, which measured values were registered by way of an imaging system. In at least one embodiment, the method includes at least: generating an at least three-dimensional data record from the measured values; analyzing the at least three-dimensional data record and generating parameter maps in respect of at least two of the following parameters: thickness and/or change in thickness of a myocardial wall, movement of the myocardial wall, local blood-supply values for defined spatial regions of the heart; automatically generating a results parameter map on the basis of the generated parameter maps according to fixed rules; and outputting the results parameter map. Moreover, at least one embodiment of the invention relates to a correspondingly designed device.

20 Claims, 5 Drawing Sheets

METHOD AND DEVICE FOR POST-PROCESSING MEASURED VALUES REGISTERED BY WAY OF AN IMAGING SYSTEM

PRIORITY STATEMENT

The present application hereby claims priority under 35 U.S.C. §119 on German patent application number DE 10 2009 032 442.9 filed Jul. 9, 2009, the entire contents of which are hereby incorporated herein by reference.

FIELD

At least one embodiment of the present invention generally relates to a method for post-processing measured values registered by means of an imaging system. At least one embodiment also generally relates to a device for the same purpose.

BACKGROUND

These days, modern medical imaging systems such as, for example, magnetic resonance systems, computed tomography scanners, PET or SPECT systems, ultrasound equipment, etc. are able to supply very large amounts of image data at a high resolution from measured values. A challenge for improving the application of such imaging systems and the results obtained thereby therefore also consists of processing the large number of measured values and outputting the latter for a diagnosis and/or intervention planning such that the person diagnosing or the planner can recognize all relevant information.

Computed tomography has established itself as an imaging method in the medical sector. This method is based on emitting X-ray radiation through an examination object, e.g. through a human body, in which the location of the emission of the X-ray radiation, i.e. an X-ray source for example, is rotated around the examination object. A sensor apparatus on the same orbit with respect to the examination object is rotated opposite to the location of the emission of the X-ray radiation, and so the sensor apparatus registers the X-ray radiation penetrating the examination object. This results in measured values, for example in the form of raw image data or measured values derived from analyzing raw image data or processed raw image data, from which three-dimensional image data records can be generated by way of an image post-processing method. This means that the image data records represent and image the spatial structure of an examination region, i.e. a tissue region, for example.

In a development, a plurality of three-dimensional image data records of the same examination region, which were recorded with a time offset with respect to one another, can be combined in a sequence of steps, and so this results in a four-dimensional image data record that illustrates the development of an examination region over time. Thus, this is a so-called multi-phase three-dimensional data record, which is also referred to as a "movie".

By way of example, such four-dimensional data records are used for imaging the heart, more particularly the myocardium, that is to say the heart muscle, wherein the procedure data can for example illustrate the cyclical change in the wall thickness and the cyclical wall movement, as well as the blood supply of the heart. By way of example, this allows the detection of pathological wall-movement disorders, which can for example be caused by a dangerous stenosis of a coronary artery.

A problem in cardiac imaging with the aid of three- or four-dimensional image data records is that pathological structures can only be recognized reliably if a multiplicity of aspects, such as for example the wall thickness, the cyclical variation thereof over time, the wall movement and the blood supply, are taken into account. This requires much specialist knowledge and much experience of the operator during the evaluation of the measured values.

In order to diagnose pathological wall-movement disorders, specialists still have to consider independently of one another all parameters in connection with the wall movement and further parameters of the function of the heart. This is connected to higher risks and moreover this is connected to significant time expenditure. Finally, the dependence on the evaluating person leads to lower reproducibility of the examinations. This is problematic particularly if comparison measurements are to be performed in order to follow the temporal profile of the change of tissue structures or the reaction thereof to certain therapeutic measures. Likewise, cross-comparison studies, in which the evaluation results from different patients or subjects are intended to be compared, only have a diagnostic value of limited reliability, should they even be possible.

SUMMARY

At least one embodiment of the present invention provides, as a basis for improved diagnostic processes, diagnosis auxiliary methods/devices in the form of a method and a device for post-processing measured values, by which method and device at least one of the aforementioned disadvantages are avoided.

Accordingly, a method according to at least one embodiment of the invention for post-processing measured values of a tissue region comprising at least part of a heart, which measured values were registered by means of an imaging system, comprises at least the following method steps:
  generating an at least three-dimensional data record, preferably an image data record, from the measured values,
  analyzing the at least three-dimensional data record and generating parameter maps in respect of at least two of the following parameters:
    thickness and/or change in thickness of a myocardial wall,
    movement of the myocardial wall,
    local blood-supply values for defined spatial regions of the heart,
  automatically generating a results parameter map on the basis of the generated parameter maps according to fixed rules, which are preferably stored in a post-processing protocol,
  outputting the results parameter map, for example to a database and/or a different type of storage and/or a user with the aid of a visualization apparatus, i.e. for example a monitor or a printer.

All values derived directly or indirectly from a measurement by an imaging system are understood to be measured values within the scope of the method, e.g. image measured values of individual pixels and/or voxels with different spatially-dependent intensities. This is used to generate a data record having a spatial, i.e. three-dimensional, data cover.

This data record is analyzed in respect of at least two of the aforementioned parameters, preferably in respect of all the aforementioned parameters, wherein the spatial regions of the heart can extend in one as well as two or even in all three spatial dimensions. The results of this parameter analysis are then provided in the form of parameter maps.

By way of example, so-called polar maps can be used as parameter maps, i.e. schematic spatially resolved summaries of three- or four-dimensional data records in which individual aspects such as the wall thickness, wall movement or blood supply are prepared graphically for an operator. By way of example, polar maps can be presented on the basis of the so-called AHA 17 segment grid, in which cardiac segments are determined in a plurality of predefined slice planes of the heart and displayed around one another in an annular fashion. Another option for the display is the 20-segment grid, as is used, for example, in SPECT (single proton emission computed tomography) nuclear cardiology. However, the parameter mapping can also be performed on the basis of slice images or in a three-dimensional image of the tissue derived directly from the tissue structure, for example with the aid of corresponding color-coding. What is decisive is that coding on the basis of the determined parameter values is undertaken with the help of a suitable display surface representing the cardiac tissue.

The parameter maps generated in this fashion are now processed further into one or more results parameter map(s) according to fixed rules. Here, the generated parameter maps are suitably combined with one another, wherein the fixed rules are preferably fixed in advance but can however also be modified during the method when required, for example by means of an additional user input, which for example contains interest of a user in particular findings. Thus, the post-processing protocol contains such rules for combining the generated parameter maps. In particular, these rules preferably contain rules for weighting the generated parameter maps relative to one another and rules for deriving the display modes of the results parameter map(s). The results parameter map generated in this fashion is finally output for further use.

A significant use of the method according to at least one embodiment of the invention can be considered that of providing compressed coded information from the measured values, which information allows an overview of analysis results. With the aid of such combined information, generated as a result of the rules fixed in the post-processing protocol, a general view or at least a compressed partial general view is presented to the user, with the aid of which said user can reproducibly evaluate measured values or data records, and relate these to one another. In end effect, this type of post-processing of the measured value lifts the result from a micro-observation plane to a macro- or even meta-plane, in which information is presented in respect of a plurality of considered parameters, preferably in respect of all considered parameters.

Thus, the method uses processes on the basis of measured values from an imaging system whose processes are automated as far as possible and preferably automated completely. Such imaging systems should be understood to be all types of tomography scanners such as computed tomography scanners, magnetic resonance imaging scanners or similar radiological systems, i.e. ultrasound equipment and the like as well.

Accordingly, a device according to at least one embodiment of the invention for post-processing measured values of a tissue region comprising at least part of a heart, which measured values were registered by way of an imaging system, has:

- a measured-value input interface for adopting the measured values and a generation unit for generating an at least three-dimensional data record from the measured values and/or
- an input interface for an at least three-dimensional data record, as well as

- an analysis unit designed for analyzing the at least three-dimensional data record and generating parameter maps in respect of at least two of the following parameters:
    thickness and/or change in thickness of a myocardial wall,
    movement of the myocardial wall,
    local blood-supply values for defined spatial regions of the heart,
- a parameter combining unit for automatically generating results parameter maps on the basis of the generated parameter maps, wherein the parameter combining unit is connected to a storage apparatus, which storage apparatus maintains a post-processing protocol with fixed rules,
- an output interface for outputting the results parameter maps.

Thus, analogously to at least one embodiment of the method, at least one embodiment of the device has units designed for the post-processing. The aforementioned interfaces do not necessarily have to be designed as hardware components, but can also be implemented as software modules, for example if the measured values can be adopted by another component, such as for example an image reconstruction device or the like, implemented in the same instrument or only have to be transmitted to this other component by way of software. Likewise, the interfaces can also consist of hardware and software components, such as for example a standard hardware interface that was specifically configured by software for the particular use.

In the present case, the storage apparatus can be arranged within the device, but also outside it, wherein, in the latter case, the storage apparatus is linked to the device or the parameter combining unit via an input interface. It can be designed as an independent unit or as a portion of a larger storage apparatus and/or comprise a plurality of subcomponents, which can then also be arranged partly within and partly outside of the device.

Overall, a majority of the components for implementing the device in accordance with at least one embodiment of the invention, more particularly the generation unit, the analysis unit and the parameter combining unit, can wholly or partly be implemented in the form of software modules on a processor.

Thus, at least one embodiment of the invention also comprises a computer program product, which can be loaded directly into a storage of a programmable image-processing apparatus, with program-code segments for executing all steps of a method according to at least one embodiment of the invention if the computer program product is executed on the image-processing apparatus.

At least one embodiment of the invention moreover comprises an imaging system with a device according to at least one embodiment of the invention. Such an imaging system also comprises, in addition to a recording unit for recording images, a diagnosing station, which can be arranged spatially separate from the recording unit and/or the device according to at least one embodiment of the invention. The device according to at least one embodiment of the invention is preferably designed as part of such a diagnosing station.

Further particularly advantageous refinements and developments of at least one embodiment of the invention also emerge from the dependent claims and the following description. Here, the device according to at least one embodiment of the invention can also be developed according to the present claims in respect of the method.

The local blood-supply values preferably comprise local probability values on the basis of stenosis values in supply and/or discharge vessels of the heart. Such stenosis values for example represent the degree of through-flow through a coronary artery in the region of a stenosis or the narrowing of the lumen of this artery, for example by specifying the percentage of the local diameter and/or the lumen cross-sectional area. They approximately represent the risk of a supply shortage or a complete block, which risk results from a stenosis and can thus be included in the results parameter map as a type of risk factor. In addition to this type of blood-supply values, alternatively or additionally, it is also possible for use to be made of other blood-supply values, for example values that were obtained with the aid of a temporally resolved blood-perfusion measurement.

Within the scope of the method according to at least one embodiment of the invention, it is particularly preferred for use to be made of a four-dimensional data record, which includes a temporal sequence of steps. In particular, when the focus is on displaying movements, more particularly superposed movements such as changes in the wall thickness and the wall movement, the inclusion of the temporal sequence component is very valuable. These superposed movements can be illustrated together in the combination of the different parameter maps without anything being lost from the essential significance of the individual measured values. Thus, the method according to at least one embodiment of the invention exhibits a particularly distinctive effect, particularly in time-resolved imaging.

The results parameter map can be generated on the basis of different analysis aspects. It preferably comprises an analysis of a deviation from the standard of standard values in at least one of the generated parameter maps, particularly preferably in all of the generated parameter maps. Such standard values can be predetermined in advance but can also relate to particular measured values from the imaging measurement to be evaluated. By way of example, normal data from preliminary examinations such as clinical studies or the like can be included. It was found to be particularly advantageous for the analysis of the deviation from the standard to comprise an analysis of the deviation from an averaging value, e.g. a median or a mean value, of the respective parameter values to be analyzed, which averaging value was determined in an averaging process. Such an averaging value produces an individual frame of reference for the specific case analysis, i.e. for the individual heart to be examined, which frame of reference can later also be used in subsequent examinations for comparison purposes.

The generation of the results parameter map preferably comprises a combination, preferably a weighted combination, particularly preferably a weighted addition, of reference values derived from the generated parameter maps. These reference values can be absolute values or values in respect of deviations from the standard. Thus, as a simplification, the generated parameter maps could be said to be "placed on top of one another", like a plurality of slides are placed on top of one another in order to obtain a combined image projection. The weighted combination is particularly preferably performed under equal weighting of the derived reference values because this constitutes the simplest procedure, which respectively assigns the same importance to each individual observation factor in the form of a parameter map, and this is currently also more or less the case in practice.

It was found to be particularly advantageous for visual representations of tissue structures to be added to the results parameter map. These representations preferably comprise information relating to supply and/or discharge organs of the heart, i.e. for example representations of a coronary artery tree. This provides both geometric and structural information of the observed tissue in addition to the analysis results. These can play an important role as navigation and detection aids, for example when assigning regions of risk to certain coronary arteries. The addition of visual representations can be brought about by complete integration, but it can also be an assignment of data from the visual representations to the results parameter map, wherein the visual representations per se are not maintained within the results parameter map, but elsewhere, for example in a database or a separate storage region.

According to a particular example embodiment of the invention, a schematic subdivision into segments based on slice planes of the heart is used as a basis for the results parameter map and/or the generated parameter maps, for example the aforementioned 17- or 20-segment models. What is achieved thereby is that the heart is imaged in a plurality of planes and over its entire cross section, and this is achieved to a standard that is established custom and to which users can therefore relate to in a significantly simpler fashion when they now wish to analyze new parameter maps in the form of results parameter maps. Moreover, the subdivision into segments simplifies the local assignment of regions of the myocardial wall to map sections.

As an alternative, or in addition, provision can furthermore advantageously be made for a subdivision based on supply regions of the heart defined by supply organs to be used as a basis for the results parameter map and/or the generated parameter maps, the boundaries of which subdivisions are preferably integrated at least into the results parameter map or linked to the latter. Ultimately, this means that the results parameter map and, where possible, the generated parameter maps as well have as their bases an individual representation of the imaged heart. Thus, by way of example, supply regions of the myocardium can be determined due to the large coronary arteries, namely the right coronary artery (RCA) and the left coronary artery with its two individual strands, known by the abbreviations LCX (left circumflex) and LAD (left anterior descending), preferably on the basis of the shortest Euclidean distance between a tissue and a coronary artery, which can serve as subdivision of the heart. The illustration of the demarcation between these supply regions quickly and effectively shows a user how to be able to assign a conspicuity discovered in the results parameter map. This once again allows significantly clearer conclusions to be drawn in respect of the severity or meaning of conspicuities.

In principle, all types of map illustrations within the scope of the method according to at least one embodiment of the invention are suitable as parameter maps, that is to say, for example, discrete parameter maps as well in which entire illustration segments based on threshold values are only illustrated in certain clearly delimited colors. Parameter maps with a continuous display spectrum are particularly preferably used as parameter maps, preferably also as a results parameter map, because they can make more precise statements and can therefore be used more easily in combination with other parameter maps. By way of example, such a display spectrum thus comprises the entire color spectrum and/or the entire grayscale spectrum, wherein each pixel of the respective illustration is assigned its own color value. By way of example, a parameter map for the perfusion of the myocardium can thus illustrate more strongly perfused regions with higher red color intensity. Furthermore, it is also possible to combine parameter maps illustrated in gray with those having a color resolution, or also to combine parameter maps illustrated in gray into a color-resolved results parameter map, or vice versa.

BRIEF DESCRIPTION OF THE DRAWINGS

In the following text, the invention will once again be explained in more detail on the basis of example embodiments and with reference to the attached figures. Here, equivalent components are provided with identical reference signs in the various figures, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
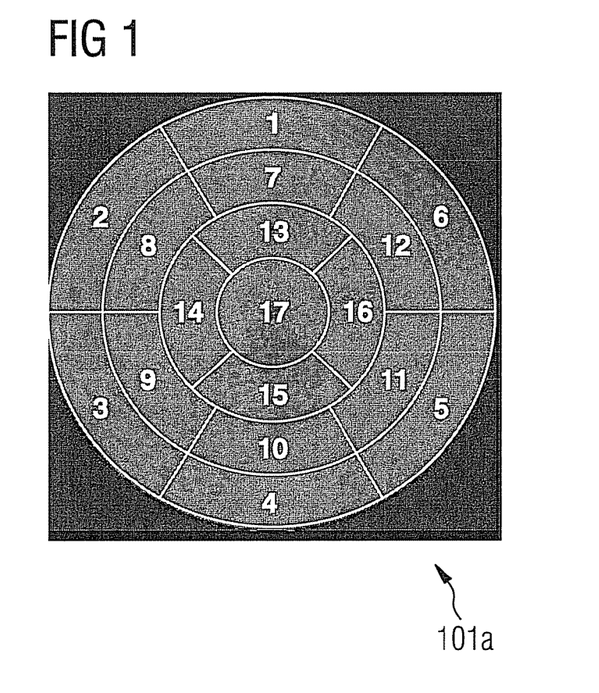
FIG. 1 shows an example illustration of a first parameter map, as can be generated within the scope of a method according to an embodiment of the invention.
Figure 2:
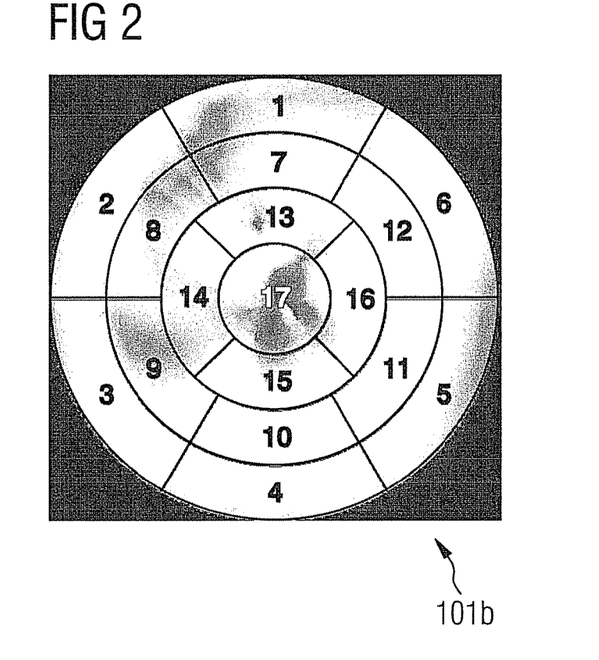
FIG. 2 shows an example illustration of a second parameter map, as can be generated within the scope of a method according to an embodiment of the invention.
Figure 3:
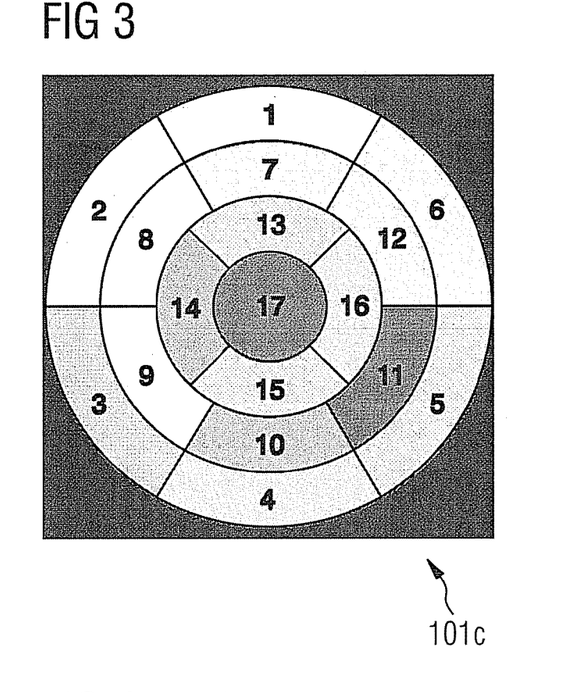
FIG. 3 shows an example illustration of a third parameter map, as can be generated within the scope of a method according to an embodiment of the invention.

FIGS. 1, 2 and 3 show three parameter maps 101$a$, 101$b$, 101$c$ in the form of polar maps of a human heart, which were each generated under different analysis aspects. All images, including the following ones, are generated on the basis of the segment subdivision of the AHA 17-segment grid. This means that the circular segment 17 lying in the center represents a slice plane at the upper end of the heart, the row of four segments 13, 14, 15, 16 arranged around it represent so-called apical segments of a slice plane in the upper half of the heart, the row of six segments 7, 8, 9, 10, 11, 12 arranged around them represent so-called mid-cavity segments of a slice plane in the lower half of the heart and the segments 1, 2, 3, 4, 5, 6 arranged around them represent so-called basal segments from a slice plane in the lower region of the heart.

The parameter map 101a in FIG. 1 is a so-called first pass enhancement polar map, i.e. a polar map in which the distribution of a contrast-agent enhancement in a myocardium is illustrated. It can be assumed that regions appearing darker in the parameter map 101a are not perfused as well as other regions. On its own, the information that can be gathered from this polar map 101a has relatively little value because essential references for a user, more particularly more precise references to supply or discharge vessels, are missing.

In FIG. 2, the parameter map 101b refers to the change over time in the wall thickness of the same myocardial wall as in FIG. 1. Here, darker regions in the image represent zones of a lower change in wall thickness compared to the average change in wall thickness in this heart. Similarly, it is also possible for the wall thickness itself or other parameters to be illustrated. Again, there is a lack of further references that could significantly improve the statement of this polar map.

Both parameter maps 101a and 101b are so-called continuous polar maps in which different color or grayscale values are used next to one another within a segment. They are particularly suitable for combining in a results parameter map, since nuances can be expressed in an improved fashion here as a result of the color shading. By contrast, FIG. 3 shows in an example fashion a parameter map 101c in the form of a discrete polar map. Here, only one color or grayscale value is provided in each case for each segment of the segment grid, wherein the color or grayscale value was determined on the basis of a thresholding method. Such discrete polar maps can also be used within the scope of the method, and both types of polar maps can also be combined with one another. The parameter map 101c schematically shows the result of analyzing the wall movement of the same heart, the analysis results of which are shown in FIGS. 1 and 2. Here, regions with wall movements that are stronger than the mean of the wall movement are coded by darker grayscale values.

Figure 4:
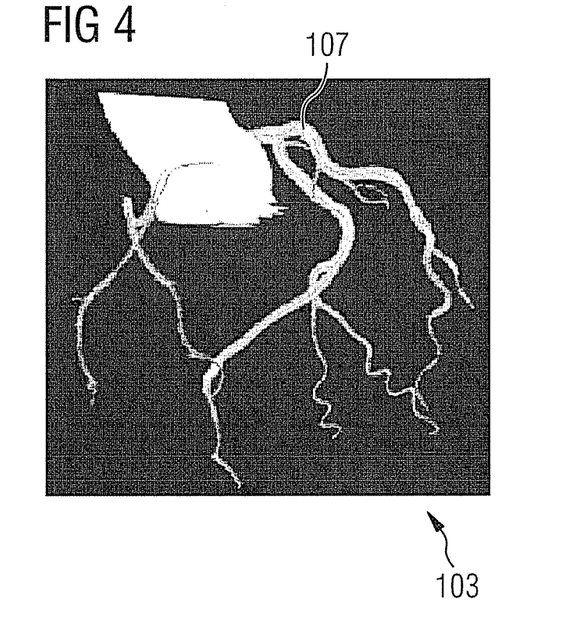
FIG. 4 shows an image display of a human coronary tree segmented from image data of cardiac tissue.

FIG. 4 shows a human coronary tree 103 with a plurality of coronary arteries 107, segmented from image data of cardiac tissue, as can for example be derived from image data from a computed tomography scanner. The positions of the branchings of the coronary tree 103 are patient-dependent, as are their profiles along the heart, not least due to the different heart sizes. By contrast, the AHA 17-segment model does not take into account such individual deviations, which can be significant.

It only becomes particularly evident as a result of this illustration that important information about the state of a myocardium cannot be read off a single polar map. Rather, a user must ultimately study a number of such images and independently relate them to one another.

Figure 5:
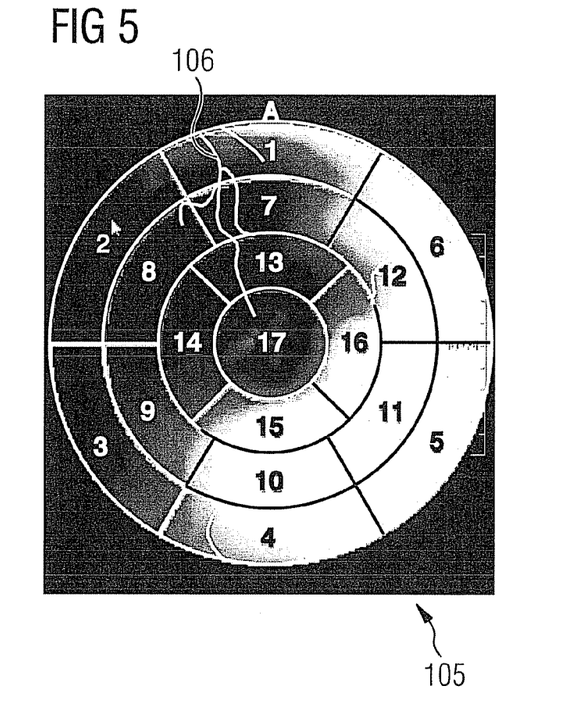
FIG. 5 shows a first example embodiment of a results parameter map as a result of an example of a method according to an embodiment of the invention.

FIG. 5 shows a possible result of a method according to an example embodiment of the invention in the form of a results parameter map 105. In order to generate the latter, the three parameter maps 101a, 101b, 101c were combined by weighted addition with respectively equal weighting of each parameter map 101a, 101b, 101c. In this combined polar map 105, grayscale values are illustrated in the segment grid, which grayscale values represent coded combined information in respect of wall thickness, change in wall thickness, wall movement and blood supply. The darker a region is illustrated in this results parameter map 105, the more the combined indicators indicate low activity and worse perfusion. In order now to be able to bring about an assignment to the coronary arteries 107 (cf. FIG. 4), the vessel profiles 106 of the three main coronary arteries were also fitted into the results parameter map, i.e. superposed onto the image. It can be seen that a tendentiously undersupplied and little-moved region of the myocardium corresponds to the region of the coronary artery arranged top left. By way of example, a user can thus derive from this illustration that supply problems are probably due to this coronary artery and the relative inactivity of the myocardium could for example be lifted by targeted treatment of this vessel.

Figure 6:
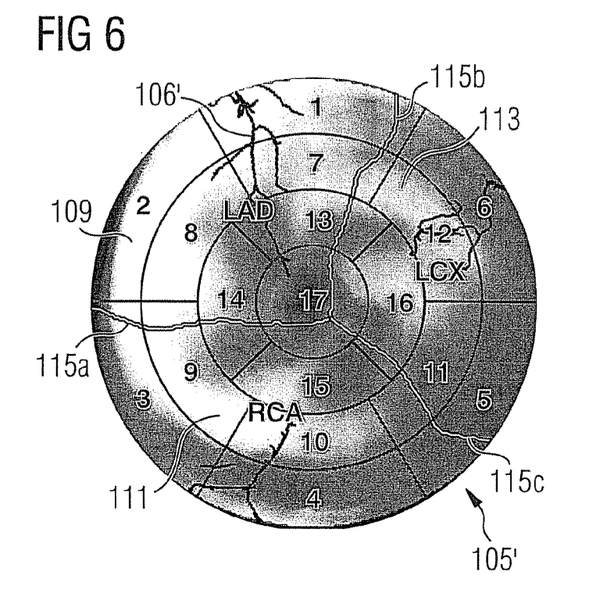
FIG. 6 shows a second example embodiment of a results parameter map as a result of an example of a method according to an embodiment of the invention.

FIG. 6 shows a second example embodiment of a results parameter map 105'. Here too, combined parameter analysis values and vessel profiles 106' (however, from a different heart in this case) are illustrated in the already known AHA 17-segment grid on the basis of grayscale values, have been combined analogously to the generation of the parameter map 105 in FIG. 5. Boundaries 115a, 115b, 115c of supply regions 109, 111, 113 are additionally plotted as assignment criteria for image evaluation. This information is maintained in a separate file and superposed over the parameter map 105'. These supply regions 109, 111, 113 relate to the supply of tissue by the three main arteries RCA, LAD, LCX; their boundaries are determined by the shortest Euclidean distance from the closest supply organ. This individual assignment of supply regions 109, 111, 113 allows pathological conspicuities of the myocardium to be related to the coronary arteries in an even easier fashion. The user thus obtains added value in the form of combination information that allows further simplification or refinement of the appraisal of the situation.

Figure 7:
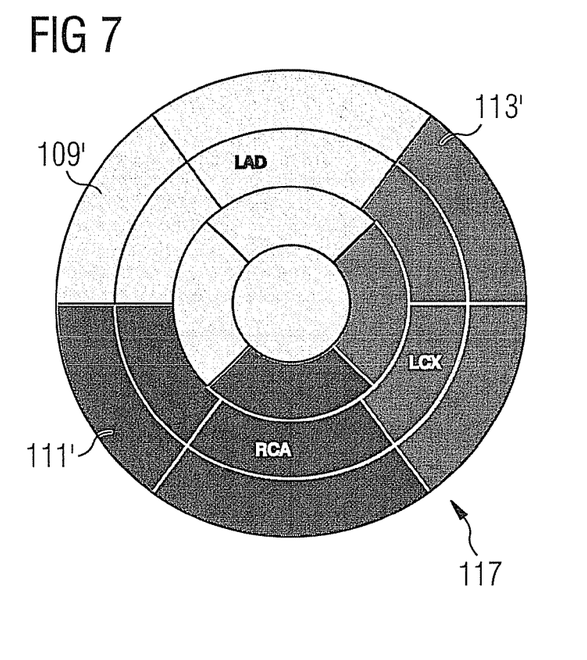
FIG. 7 shows a segment grid with a frame of reference for assigning segments to individual supply regions, derived from the illustration in FIG. 6.

FIG. 7 shows a parameter map 117 with a segment grid as a frame of reference for assigning segments to individual supply regions, derived from the illustration in FIG. 6. Here, the assignment regions 109, 111, 113 are resolved in schematic assignment regions 109', 111', 113' and so an individual supply situation is illustrated schematically in the segment grid system. Such a polar map, which is shown here to clarify the meaning of assignment regions, can within the scope of the invention be integrated into a results parameter map 105, 105', for example by virtue of the fact that the color or grayscale values are stored as background of a results parameter map 105, 105'.

Figure 8:
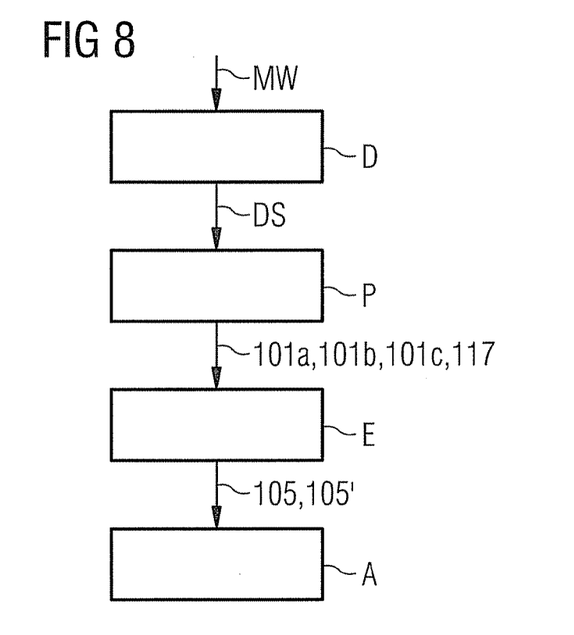
FIG. 8 shows a schematic block diagram of the procedure of an embodiment of a method according to an embodiment of the invention.

FIG. 8 shows a schematic block diagram of the procedure of an embodiment of a method according to an embodiment of the invention. In the process, an at least three-dimensional, preferably four-dimensional (i.e. resolved in time), (image) data record DS is generated from measured values MW from an imaging system in a step D, for example within an image reconstruction.

In a step P, the data record DS is analyzed in respect of a plurality of parameters and parameter maps 101a, 101b, 101c, 117 are generated in respect thereof, which parameter maps represent, as explained above, the development of contrast-agent enrichment in a myocardium, the change in the wall thickness of the myocardium and the wall movement thereof, and schematic supply regions.

Then a results parameter map 105, 105', as explained and illustrated in conjunction with FIGS. 5 and 6, is generated automatically in a method step E on the basis of the parameter maps 101a, 101b, 101c, 117. This is brought about according to rules fixed in a post-processing protocol. Finally, the results parameter maps 105, 105 are output in a step A.

Figure 9:
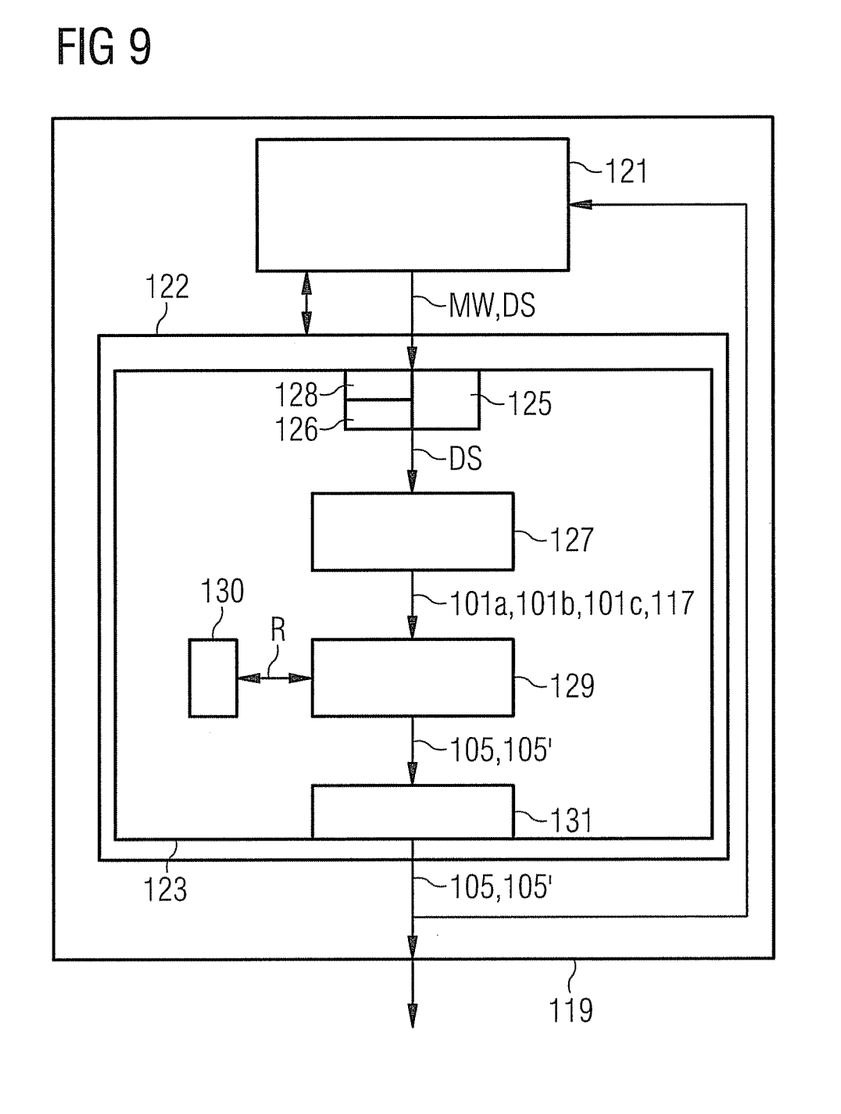
FIG. 9 shows a schematic block diagram of the components of an imaging system according to the invention with an example embodiment of a device according to an embodiment of the invention.

FIG. 9 shows a schematic block diagram of an imaging system 119 according to an embodiment of the invention with an image recording unit 121 and a diagnosing station 122, within which an example embodiment of a device 123 according to an embodiment of the invention is arranged. Such a device 123 can also be implemented outside of a diagnosing station, for example on a separate calculation unit. A number of further components of imaging systems have not been illustrated for reasons of clarity and are sufficiently well-known to a person skilled in the art.

The device 123 comprises an input interface 125 for three-dimensional or four-dimensional data records DS and a measured-value input interface 128 combined with a generation unit 126 for data records DS from measured values. The generation unit 126 generates three-dimensional data records from measured values MW, i.e. for example from raw image data from an imaging unit, that is to say it is a reconstruction unit. This allows both pure measured values MW and three-dimensional data records DS derived therefrom to be accepted and possibly processed further. The device 123 furthermore comprises an output interface 131 for outputting results parameter maps 105, 105 and an analysis unit 127 and a parameter combining unit 129 arranged between the input interfaces 125, 128 and the output interface 131.

Here, the analysis unit 127 is designed such that it analyzes the at least three-dimensional data record DS and generates parameter maps 101a, 101b, 101c, 117 as illustrated in FIGS. 1, 2, 3 and 7. The parameter combining unit 129 is connected to a storage apparatus 130, which maintains a post-processing protocol with fixed rules R. Herein, it is fixed that the parameter maps 101a, 101b, 101c, 117 are combined with one another by virtue of the fact that they are added with the same weighting. Results parameter maps 105, 105' emerge from this addition.

Finally, reference is once again made to the fact that the method described in detail above and the illustrated device and the imaging system are merely example embodiments that can be modified in a variety of ways by a person skilled in the art without departing from the scope of the invention. For completeness' sake, reference is also made to the fact that the use of the indefinite article "a" or "an" does not preclude the relevant features from also being able to be present a number of times. Likewise, the term "unit" or "module" does not preclude these from consisting of a plurality of components that can, if applicable, also be distributed in space.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:
1. A method for post-processing measured values of a tissue region comprising at least part of a heart, the measured values being registered by way of an imaging system, the method comprising:
  generating, by the imaging system, an at least three-dimensional data record from the measured values;
  analyzing, by the imaging system, the at least three-dimensional data record and generating at least two parameter maps, each of the generated parameter maps being polar maps generated based on at least two of, at least one of thickness and change in thickness of a myocardial wall, movement of the myocardial wall, and local blood-supply values for defined spatial regions of the heart;

automatically, by the imaging system, generating a results parameter map by combining the at least two generated parameter maps according to fixed rules; and outputting, by the imaging system, the results parameter map.

2. The method as claimed in claim 1, wherein the local blood-supply values comprise local probability values on the basis of stenosis values in at least one of supply and discharge vessels of the heart.

3. The method as claimed in claim 2, wherein of the at least three-dimensional data record includes a four-dimensional data record, which includes a temporal sequence of steps.

4. The method as claimed in claim 1, wherein of the at least three-dimensional data record includes a four-dimensional data record, which includes a temporal sequence of steps.

5. The method as claimed in claim 1, wherein the generation of the results parameter map comprises an analysis of a deviation from the standard of standard values in at least one of the generated parameter maps.

6. The method as claimed in claim 5, wherein the generation of the results parameter map comprises an analysis of a deviation from the standard of standard values in all generated parameter maps.

7. The method as claimed in claim 6, wherein the analysis of the deviation from the standard comprises an analysis of the deviation from an averaging value.

8. The method as claimed in claim 5, wherein the analysis of the deviation from the standard comprises an analysis of the deviation from an averaging value.

9. The method as claimed in claim 1, wherein the generation of the results parameter map comprises a combination of reference values derived from the generated parameter maps.

10. The method as claimed in claim 9, wherein the combination is performed under equal weighting of the derived reference values.

11. The method as claimed in claim 9, wherein the combination comprises a weighted combination.

12. The method as claimed in claim 11, wherein the weighted combination comprises a weighted addition.

13. The method as claimed in claim 12, wherein the weighted combination is performed under equal weighting of the derived reference values.

14. The method as claimed in claim 1, wherein visual representations of tissue structures are added to the results parameter map, which representations comprise information relating to at least one of supply and discharge organs of the heart.

15. The method as claimed in claim 1, wherein a schematic subdivision into segments based on slice planes of the heart is used as a basis for at least one of the results parameter map and the generated parameter maps.

16. The method as claimed in claim 1, wherein a subdivision based on supply regions of the heart defined by supply organs is used as a basis for at least one of the results parameter map and the generated parameter maps, the boundaries of which subdivision are integrated at least into the results parameter map or linked to the latter.

17. The method as claimed in claim 1, wherein parameter maps with a continuous display spectrum are used as parameter maps.

18. A device for post-processing measured values of a tissue region comprising at least part of a heart, the measured values being registered by way of an imaging system, the device comprising:

at least one of (1) a measured-value input interface configured to adopt the measured values and a generation unit configured to generate an at least three-dimensional data record from the measured values, and (2) an input interface for inputting the at least three-dimensional data record;

an analysis unit configured to analyze the at least three-dimensional data record and to generate at least two parameter maps, each of the generated parameter maps being polar maps generated based on at least two of, at least one of thickness and change in thickness of a myocardial wall, movement of the myocardial wall, and local blood-supply values for defined spatial regions of the heart;

a parameter combining unit to automatically generate results parameter maps by combining the at least two generated parameter maps, wherein the parameter combining unit is connected to a storage apparatus, the storage apparatus being usable to maintain a post-processing protocol with fixed rules; and an output interface to output the results parameter maps.

19. An imaging system including a device for post-processing measured values of a tissue region comprising at least part of a heart, the measured values being registered by way of an imaging system, the device comprising:

at least one of (1) a measured-value input interface configured to adopt the measured values and a generation unit configured to generate an at least three-dimensional data record from the measured values, and (2) an input interface for inputting the at least three-dimensional data record;

an analysis unit configured to analyze the at least three-dimensional data record and to generate at least two parameter maps, each of the generated parameter maps being polar maps generated based on at least two of, at least one of thickness and change in thickness of a myocardial wall, movement of the myocardial wall, and local blood-supply values for defined spatial regions of the heart;

a parameter combining unit to automatically generate results parameter maps by combining the at least two generated parameter maps, wherein the parameter combining unit is connected to a storage apparatus, the storage apparatus being usable to maintain a post-processing protocol with fixed rules; and an output interface to output the results parameter maps.

20. A computer program product, loadable directly into a storage of a programmable image-processing apparatus for post-processing measured values of a tissue region including at least part of a heart, the measured values being registered by way of an imaging system, comprising:

program-code segments stored in the computer program product configured to perform a method when executed on the image-processing apparatus, the method including, generating, by the imaging system, an at least three-dimensional data record from the measured values;

analyzing, by the imaging system, the at least three-dimensional data record and generating at least two parameter maps, each of the generated parameter maps being polar maps generated based on at least two of, at least one of thickness and change in thickness of a myocardial wall, movement of the myocardial wall, and local blood-supply values for defined spatial regions of the heart;

automatically, by the imaging system, generating a results parameter map by combining the at least two generated parameter maps according to fixed rules; and outputting, by the imaging system, the results parameter map.

* * * * *